(12) United States Patent
Humphreys

(10) Patent No.: US 7,244,587 B2
(45) Date of Patent: Jul. 17, 2007

(54) EXPRESSION VECTORS ENCODING BACTERIOPHAGE SIGNAL PEPTIDES

(75) Inventor: David Paul Humphreys, Maidenhead (GB)

(73) Assignee: Celltech R&D Limited, Slough, Berkshire (GB)

( * ) Notice: Subject to any disclaimer, the term of this patent is extended or adjusted under 35 U.S.C. 154(b) by 0 days.

(21) Appl. No.: 10/483,008

(22) PCT Filed: Jul. 5, 2002

(86) PCT No.: PCT/GB02/03129

§ 371 (c)(1),
(2), (4) Date: Aug. 4, 2004

(87) PCT Pub. No.: WO03/004636

PCT Pub. Date: Jan. 16, 2003

(65) Prior Publication Data

US 2004/0259210 A1    Dec. 23, 2004

(30) Foreign Application Priority Data

Jul. 5, 2001  (GB)  ................................. 0116460.7

(51) Int. Cl.
C12P 21/06  (2006.01)
C12N 1/20  (2006.01)
C12N 15/00  (2006.01)
C07H 21/04  (2006.01)

(52) U.S. Cl. ............................... 435/69.1; 435/252.33; 435/320.1; 536/23.53; 536/23.1

(58) Field of Classification Search ...................... None
See application file for complete search history.

(56) References Cited

U.S. PATENT DOCUMENTS 6,476,198 B1   11/2002   Kang

FOREIGN PATENT DOCUMENTS

WO    WO97/01580    1/1997

OTHER PUBLICATIONS

Atwell et al., Mol. Immunol., vol. 33, No. 17/18, pp. 1301-1312, 1996.*

Atlan and Portalier, "Optimized extracellular production of alkaline phosphatase by lky mutants of *Escherichia coli* K12," Appl. Microbiol. Biotechnol. (1984) 19:5-12.
Forgini-Lefebvre and Portalier, "Isolation and preliminary characterization of beta-lactamase excretory mutants of *Eschericia coli* K-12," FEMS Micrbiol. Lett. (1984) 21:323-328.
Glover, "DNA Cloning: A Practical Approach, vol. II: Expression Systems," IRL Press (1995).
Glover, "DNA Cloning: A Practical Approach, vol. IV: Mammalian Systems," IRL Press (1995).
Gray, et al., "Periplasmic production of correctly processed human growth hormone in *Escherichia coli*: natural and bacterial signal sequences are interchangeable," Gene (1985) 39:247-254.
Humphreys, et al., "Human protein disulfide isomerase functionally complements a dsbA mutation and enhances the yield of pactate lyase C in *Escherichia coli*," J. Biol. Chem. (1995) 270:28210-28215.
Humphreys, et al., "Coexpression of human protein disulphide isomerase (PDI) can increase the yield of an antibody Fab' fragment expressed in *Escherichia coli*," FEBS Lett. (1996) 380:194-197.
Humphreys, et al., "F(ab')2 molecules made from *Escherichia coli* produced Fab' with hinge sequences conferring increased serum survival in an animal model," J. Immunol. Methods (1998) 217:1-10.
Humphreys, et al., "High-level periplasmic expression in *Escherichia coli* using a eukaryotic signal peptide: importance of codon usage at the 5' end of the coding sequence," Protein Express. Purif. (2000) 20:252-264.
Humphreys and Glover, "Therapeutic antibody production technologies: molecules applications, expression and purification," Curr. Opin. Drug Discovery Devel. (2001) 4:172-185.
Humphreys, et al., "A plasmid system for optimization of Fab' production in *Escherichia coli*: importance of balance of heavy chain and light chain synthesis," Protein Express. Purif. (2002) 26:309-320.
Kumagai, et al., "Expression and secretion of rice alpha-amylase by *Saccharomyces cerevisiae*," Gene (1990) 94:209-216.
Markland, et al., "Design, construction and function of a multicopy display vector using fusions to the major coat protein of bacteriophage M13," Gene (1991) 109:13-19.
Sambrook and Fritsch, "Molecular Cloning: A Laboratory Manual," 2nd ed., Cold Spring Harbor Press, New York (1989).

* cited by examiner

*Primary Examiner*—Nancy Vogel
(74) *Attorney, Agent, or Firm*—Doreen Yatko Trujillo; Cozen O'Connor, P.C.

(57) ABSTRACT

Expression vectors encoding bacteriophage signal peptides are described. The vectors may be used for the heterologous expression and secretion of polypeptides such as antibodies in bacterial host cells.

15 Claims, 4 Drawing Sheets

A) Alkaline phosphatase expression cassette
B) scFv expression cassette
C) Fab' expression construct

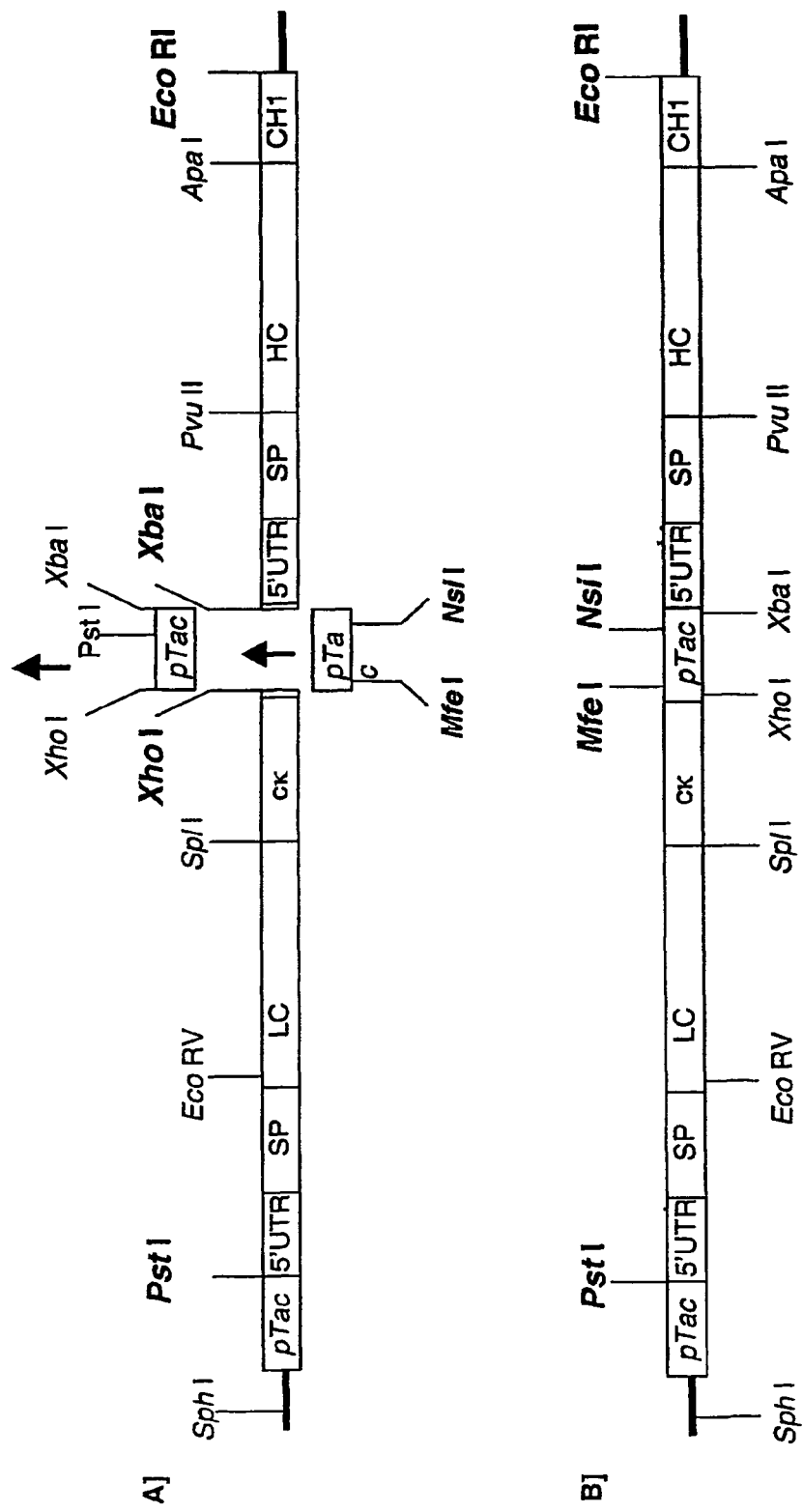
FIGURE 2 Constructs to enable the production of Fab'- signal peptide libraries

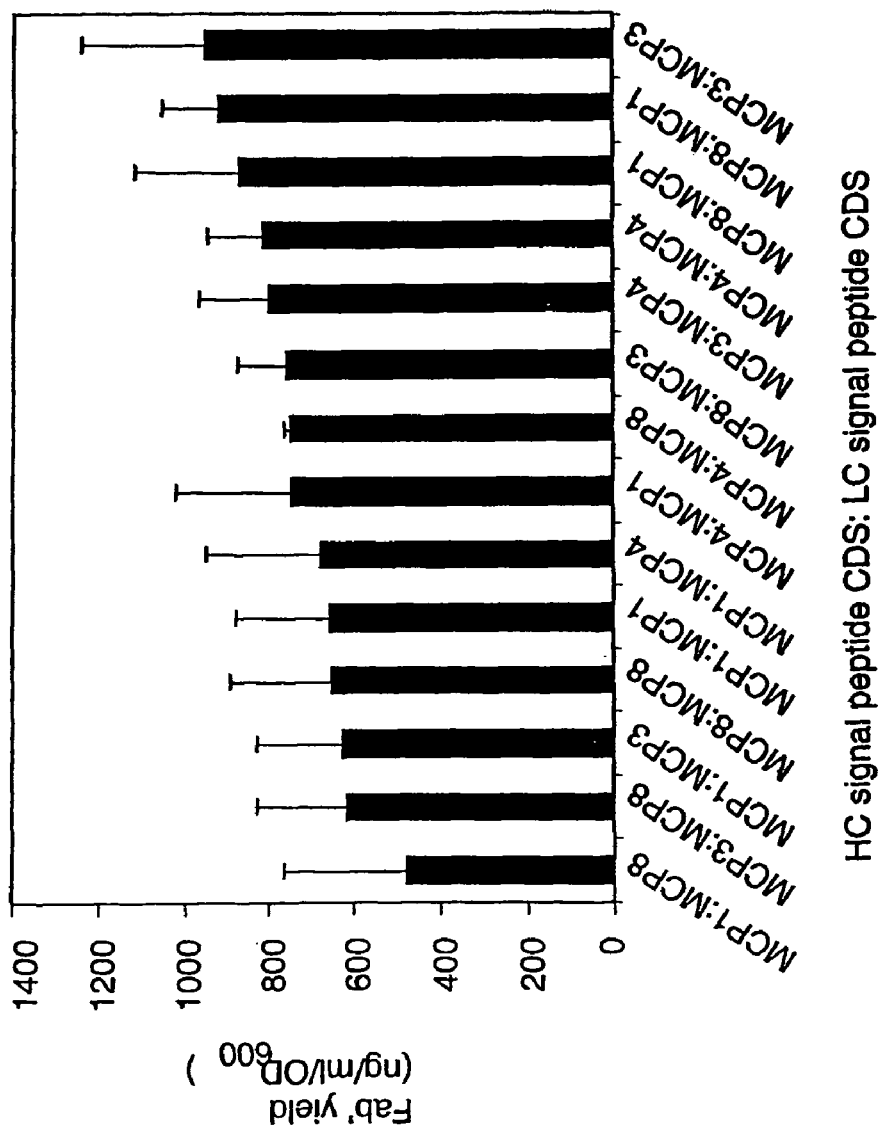
FIGURE 3  Yield of Fab' 165 from constructs with different signal peptide coding sequences in front of Heavy and Light chains

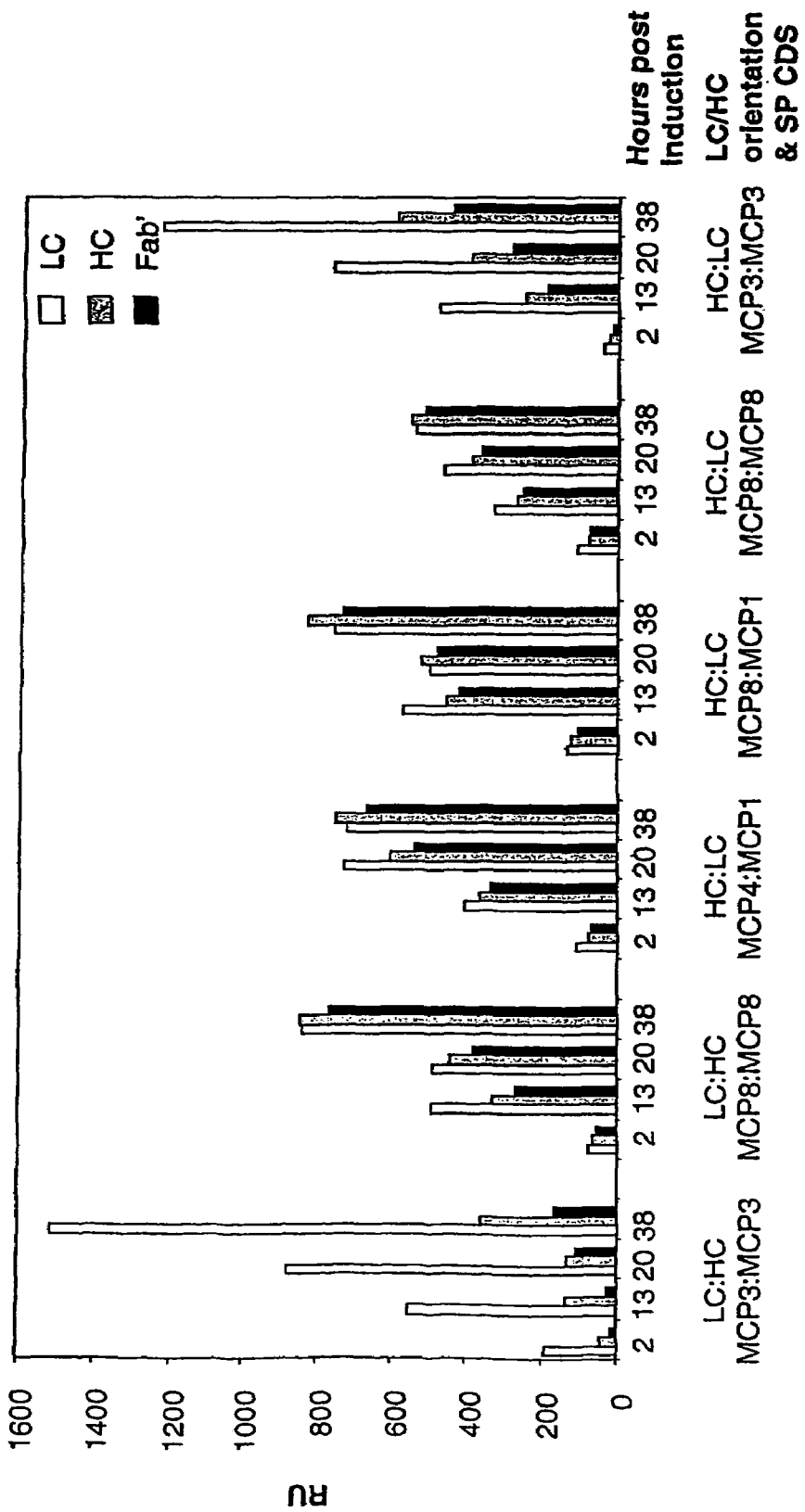

SEQUENCE LISTING

<160> NUMBER OF SEQ ID NOS: 14

<210> SEQ ID NO 1
<211> LENGTH: 23
<212> TYPE: PRT
<213> ORGANISM: Bacteriophage M13
<220> FEATURE:
<221> NAME/KEY: Major coat protein signal peptide

<400> SEQUENCE: 1

Met Lys Lys Ser Leu Val Leu Lys Ala Ser Val Ala Val Ala Thr Leu
1               5                   10                  15

Val Pro Met Leu Ser Phe Ala
            20

<210> SEQ ID NO 2
<211> LENGTH: 69
<212> TYPE: DNA
<213> ORGANISM: Bacteriophage M13
<220> FEATURE:
<221> NAME/KEY: MCPn

<400> SEQUENCE: 2
atgaaaaagt ctttagtcct caaagcctct gtagccgttg ctaccctcgt tccgatgctg      60
tctttcgct                                                             69

<210> SEQ ID NO 3
<211> LENGTH: 69
<212> TYPE: DNA
<213> ORGANISM: Artificial Sequence
<220> FEATURE:
<223> OTHER INFORMATION: MCP1

<400> SEQUENCE: 3
atgaaaaaaa gcctggttct gaaagcgagc gtggcggtgg cgaccctggt gccgatgctg    60
agcttcgcg                                                           69

<210> SEQ ID NO 4
<211> LENGTH: 69
<212> TYPE: DNA
<213> ORGANISM: Artificial Sequence
<220> FEATURE:
<223> OTHER INFORMATION: MCP2

<400> SEQUENCE: 4
atgaagaaaa gtcttgtcct gaaggcgagc gtggctgtag cgacgctggt gcctatgctg    60
agtttcgca                                                           69

<210> SEQ ID NO 5
<211> LENGTH: 69
<212> TYPE: DNA
<213> ORGANISM: Artificial Sequence
<220> FEATURE:
<223> OTHER INFORMATION: MCP3

<400> SEQUENCE: 5
atgaagaaga gtcttgtgct gaaggcaagt gtggcagtgg ctacgctggt gcctatgctg    60
agttttgcg                                                           69

<210> SEQ ID NO 6
<211> LENGTH: 69
<212> TYPE: DNA
<213> ORGANISM: Artificial Sequence
<220> FEATURE:
<223> OTHER INFORMATION: MCP4

<400> SEQUENCE: 6
atgaaaaaaa gtcttgttct gaaagcaagc gtggctgtag caactcttgt ccctatgctg    60
agttttgcg                                                           69

<210> SEQ ID NO 7
<211> LENGTH: 69
<212> TYPE: DNA
<213> ORGANISM: Artificial Sequence
<220> FEATURE:
<223> OTHER INFORMATION: MCP5

<400> SEQUENCE: 7
atgaagaaaa gtcttgtact gaaagcgagt gtggcggtcg caacgctggt accaatgctg    60
agcttcgca                                                           69

<210> SEQ ID NO 8
<211> LENGTH: 69
<212> TYPE: DNA
<213> ORGANISM: Artificial Sequence
<220> FEATURE:
<223> OTHER INFORMATION: MCP6

```
<400> SEQUENCE: 8
atgaagaaga gtcttgtgct caaggcaagc gtagcggtgg cgaccctcgt gccgatgctg     60
agtttcgcg                                                             69

<210> SEQ ID NO 9
<211> LENGTH: 69
<212> TYPE: DNA
<213> ORGANISM: Artificial Sequence
<220> FEATURE:
<223> OTHER INFORMATION: MCP7

<400> SEQUENCE: 9
atgaagaaaa gtctggtact gaaggcgagt gtggcggtgg ccactctggt tccaatgctt     60
agtttcgcg                                                             69

<210> SEQ ID NO 10
<211> LENGTH: 69
<212> TYPE: DNA
<213> ORGANISM: Artificial Sequence
<220> FEATURE:
<223> OTHER INFORMATION: MCP8

<400> SEQUENCE: 10
atgaagaaga gtctggtgct gaaagcgagt gtagcggtgg caacgctggt gccgatgctg     60
agttttgcg                                                             69

<210> SEQ ID NO 11
<211> LENGTH: 69
<212> TYPE: DNA
<213> ORGANISM: Artificial Sequence
<220> FEATURE:
<223> OTHER INFORMATION: MCP9

<400> SEQUENCE: 11
atgaaaaaga gcctggtact taaggcgagt gttgcggtgg cgacgctggt cccgatgctg     60
agttttgcg                                                             69

<210> SEQ ID NO 12
<211> LENGTH: 70
<212> TYPE: DNA
<213> ORGANISM: Artificial Sequence
<220> FEATURE:
<223> OTHER INFORMATION: Primer PhoA1

<400> SEQUENCE: 12
gcgcgcgctc tgcaggtcga gttctagata acgaggcgta aaaaatgaaa caaagcacta     60
ttgcactggc                                                            70

<210> SEQ ID NO 13
<211> LENGTH: 48
<212> TYPE: DNA
<213> ORGANISM: Artificial Sequence
<220> FEATURE:
<223> OTHER INFORMATION: Primer PhoA2

<400> SEQUENCE: 13
gcgcgcgcgc ggccgctcat tatttcagcc ccagagcggc tttcatgg                  48

<210> SEQ ID NO 14
<211> LENGTH: 30
<212> TYPE: DNA
<213> ORGANISM: Artificial Sequence
```

-continued

```
<220> FEATURE:
<223> OTHER INFORMATION: Primer PhoA3

<400> SEQUENCE: 14
cggacaccag aaatgcctgt tctggaaaac                                           30
```

EXPRESSION VECTORS ENCODING BACTERIOPHAGE SIGNAL PEPTIDES

CROSS-REFERENCE TO RELATED APPLICATIONS

The present application is a national stage application of International Application No. PCT/GB02/03129, International Filing Date: 5 Jul. 2002, which claims priority to GB 0116460.7, Filing Date: 5 Jul. 2001, each of which is incorporated herein by reference in its entirety.

The present invention relates to nucleotide sequences encoding bacteriophage signal peptides, expression vectors containing such sequences and their use for the heterologous expression and secretion of polypeptides, in particular antibodies, in bacterial systems.

Throughout this application various publications are referenced by author and year. Full citations for these publications are provided following the detailed description of the invention and Examples.

Recombinant protein production has been facilitated to a large extent by the construction of expression systems that are capable of exporting the protein of interest from the cell in which it is expressed. In order to effect secretion of the recombinant product from the host cell, these expression systems utilise amino-terminal peptide extensions, or signal peptides, which are found on the majority of eukaryotic and prokaryotic proteins that are destined for export from the cytoplasm. The characterisation of a number of signal peptides from diverse sources has revealed that whilst there is little sequence homology amongst them, they do share certain functional characteristics. These common features are a positively charged amino-terminal region, a central hydrophobic core, and a more polar carboxy-terminal region that normally terminates with a signal peptidase cleavage site.

It is quite common that the signal peptides employed in such expression systems are native to the expression host, for example, the PhoA, MalB and OmpA signal peptides of *Escherichia coli* have been used extensively to secrete polypeptides to the periplasm of that organism. However, some signal peptides are capable of working even when moved between species, e.g. secretion of Human growth hormone to the *E. coli* periplasm was more efficient when the native signal peptide was employed (Gray et al, 1985), and rice α-amylase has been efficiently secreted from *Saccharomyces cerevisiae* using its native signal sequence (Kumagai et al., 1990).

Unfortunately, the efficacy of individual signal peptides in different systems is unpredictable. The process is frequently inefficient, with low yields being commonplace. In addition, problems may be encountered with the misprocessing of the signal peptide, which may be improperly removed or incompletely cleaved. Thus, there is a need for signal peptides, which can direct secretion consistently in an efficient and universal manner i.e. achieve high yields and/or accurate cleavage.

We have found, unexpectedly, that we can obtain high levels of soluble polypeptides, in particular antibodies or antigen binding fragments thereof, from prokaryotic cells when we use a bacteriophage signal sequence (for example, that of the bacteriophage M13 major coat protein) to mediate the secretory process.

Thus according to the first aspect of the invention we provide a method of producing an antibody chain, or an antigen binding fragment thereof, comprising culturing host cells containing an expression cassette, under conditions that result in expression of the antibody chain, or antigen binding fragment thereof, from the expression cassette, wherein the expression cassette comprises a first nucleic acid encoding a bacteriophage signal peptide, or a variant thereof, operably linked to and in frame with a second nucleic acid encoding the antibody chain or antigen binding fragment thereof.

Antibodies are assembled from two light and two heavy chain polypeptides, which are linked to each other through di-sulphide bonds. Thus the term "antibody chain" as used herein refers to either an antibody light chain polypeptide or an antibody heavy chain polypeptide.

The term "antigen binding fragment" as applied to an antibody chain, is herein defined as any fragment or domain of an antibody chain that is capable of binding to an antigen independently and selectively. Examples of such antigen-binding fragments, which may be expressed and secreted according to the method of the invention, include for example, $V_H$ and $V_L$ fragments, and single chain antibodies such as, for example a scFv.

According to another aspect, the method of the invention may be used to produce a whole antibody comprising full-length heavy and light chains, or fragments thereof including, for example, Fab, Fab', $F(ab')_2$, and Fv fragments This may be achieved by producing antibody light and heavy chains or appropriate fragments thereof, according to the method of the invention, in different host cells, and then allowing assembly of the appropriate chains or fragments thereof to form a whole antibody or antibody fragment after the chains have been expressed.

Alternatively a whole antibody, or fragment thereof, may be produced by introducing at least two expression cassettes into the same host cell. Each expression cassette will comprise a first nucleic acid encoding a bacteriophage signal peptide (or a variant thereof). This will be operably linked to and in frame with a second nucleic acid, which will encode an antibody heavy chain or appropriate heavy chain fragment in one expression cassette and an antibody light chain or appropriate light chain fragment in another expression cassette. Thus, heavy and light chains, or fragments thereof, may be co-expressed within the same cell and secretion of each may be mediated by a bacteriophage signal peptide. Such expression cassettes may be introduced into host cells as distinct entities that are incorporated within a single nucleic acid molecule, or alternatively they may be introduced on separate nucleic acid molecules.

Whole antibodies, which may be produced as described above, include multimeric monospecific antibodies, as well as bi-specific or multi-specific antibodies.

An antibody or antigen binding fragment thereof, expressed and secreted according to any aspect of the invention may be polyclonal or, especially monoclonal. It may belong to any immunoglobulin class and may for example be an IgG (for example IgG1, IgG2, IgG3 or IgG4), IgE, IgM or IgA antibody. It may be of animal, for example mammalian origin, for example it may be a murine rat or human antibody or an antigen binding fragment derived therefrom. Alternatively, the antibody or antigen binding fragment may be chimeric i.e. contain portions derived from different animal species. Particular examples are well documented in the literature and include CDR grafted antibodies and antigen binding fragments.

Any signal peptide of bacteriophage origin may be employed in the invention, however, it is preferred that the first nucleic acid encodes the signal peptide from the bacteriophage M13 major coat protein, or a variant thereof. The term "variant" as used herein, refers to signal peptides having substantially the same amino acid sequence as that described below for M13 major coat protein signal peptide and which are capable of functioning at least as efficiently as the native M13 signal peptide. This encompasses M13 major coat protein signal peptide derivatives that may have been modified to alter or enhance particular features such as, for example, the signal peptidase recognition site. A signal peptide that has "substantially the same amino acid sequence" is one that shares greater than 70% identity with the amino acid sequence of the M13 major coat protein signal. Preferable variants will share greater than 75% identity, more preferably greater than 80% identity and most preferably greater than 90% identity with signal peptide from the M13 major coat protein.

In order to assess the efficacy of the variant M13 major coat signal peptides, they may be used to direct the secretion of a standard polypeptide for example, β-lactamase or alkaline phosphatase. Any of the following parameters—yield, rate of accumulation, accuracy of cleavage—may then be measured and compared to those achieved by the native M13 major coat protein signal peptide when used to direct secretion of the same model polypeptide. This provides the basis of a suitable screen for signal peptides that are capable of functioning at least as efficiently, if not better than, the native M13 major coat protein signal peptide. Methods of estimating yield and/or rate of accumulation will be obvious to the skilled man and may rely on direct measurement of the polypeptide product, or alternatively they may rely on any intrinsic enzymatic activity of the polypeptide. Specific examples of such methodology are described herein in more detail, in the detailed description of the preferred embodiments.

The native bacteriophage M13 major coat protein signal peptide is 23 amino acids in length and has the amino acid sequence "MKKSLVLKASVAVATLVPMLSFA" (SEQ ID NO: 1). Due to the degeneracy of the genetic code, any one of a number of nucleotide sequences may encode a signal peptide with this sequence. Any of these nucleic acids including the native bacteriophage M13 sequence, may be employed in the invention. In fact, we have shown, by altering the nucleotide sequence but not the amino acid sequence, of the bacteriophage M13 major coat protein signal peptide, the expression and secretion of soluble proteins in *E. coli* can be optimised. Examples of such soluble proteins include enzymes (such as alkaline phosphatase); protein hormones or toxins; soluble transport, structural or contractile proteins and, in particular, antibodies.

Thus nucleic acids encoding the M13 major coat protein signal peptide, which differ in the nucleotide sequence from the wild-type M13 bacteriophage nucleic acid sequence, but do not differ in the amino acid sequence that they encode, form yet a further aspect of the invention and may also be employed in methods of the invention as described herein. The M13 major coat protein signal peptide, encoded by a nucleic acid according to this aspect of the invention may be employed as desired, to direct the secretion of a full-length soluble protein, or a fragment or domain thereof.

Nucleic acids according to this aspect of the invention may differ from the wild-type nucleotide sequence encoding the M13 major coat protein signal peptide in any number of nucleotide positions provided that the amino acid sequence that is encoded is not altered. Thus, a nucleic acid according to this aspect of the invention may only differ in sequence at a single position, or alternatively it may differ in sequence (from the wild type) in up to a maximum of approximately 31 positions. Preferably such nucleic acids will differ in nucleotide sequence from the wild type in between approximately 18 to 25 positions. More preferably nucleic acids according to this aspect of the invention will differ in sequence from the wild type at a total of 20, 21, 22, or 23 nucleotide positions.

Examples of preferred nucleic acid sequences encoding the M13 major coat protein signal peptide for use in various aspects of the invention include the native M13 nucleotide sequence (MCPn) and novel nucleotide sequences MCP1 to MCP9 given in Table 1 below. The use of a nucleotide sequence corresponding to any one of MCPn, MCP1, MCP3, MCP4, or MCP8 is particularly preferred.

TABLE 1

Nucleic acid sequences encoding the signal peptide of the M13 major coat protein.
Nucleotide sequence MCPn 5' ATGAAAAAGTCTTTAGTCCTCAAAGCCT (SEQ ID NO:2)

CTGTAGCCGTTGCTACCCTCGTTCCGATGCT

GTCTTTCGCT 3'

MCP1 5' ATGAAAAAAGCCTGGTTCTGAAAGCGA (SEQ ID NO:3)

GCGTGGCGGTGGCGACCCTGGTGCCGATGCT

GAGCTTCGCG 3'

MCP2 5' ATGAAGAAAAGTCTTGTCCTGAAGGCGA (SEQ ID NO:4)

GCGTGGCTGTAGCGACGCTGGTGCCTATGCT

GAGTTTCGCA 3'

MCP3 5' ATGAAGAAGAGTCTTGTGCTGAAGGCAA (SEQ ID NO:5)

GTGTGGCAGTGGCTACGCTGGTGCCTATGCT

GAGTTTTGCG 3'

MCP4 5' ATGAAAAAAAGTCTTGTTCTGAAAGCAA (SEQ ID NO:6)

GCGTGGCTGTAGCAACTCTTGTCCCTATGCT

GAGTTTTGCG 3'

MCP5 5' ATGAAGAAAAGTCTTGTACTGAAAGCGA (SEQ ID NO:7)

GTGTGGCGGTCGCAACGCTGGTACCAATGCT

GAGCTTCGCA 3'

MCP6 5' ATGAAGAAGAGTCTTGTGCTCAAGGCAA (SEQ ID NO:8)

GCGTAGCGGTGGCGACCCTCGTGCCGATGCT

GAGTTTCGCG 3'

MCP7 5' ATGAAGAAAAGTCTGGTACTGAAGGCGA (SEQ ID NO:9)

GTGTGGCGGTGGCCACTCTGGTTCCAATGCT

TAGTTTCGCG 3'

MCP8 5' ATGAAGAAGAGTCTGGTGCTGAAAGCGA (SEQ ID NO:10)

GTGTAGCGGTGGCAACGCTGGTGCCGATGCT

GAGTTTTGCG 3'

MCP9 5' ATGAAAAAGAGCCTGGTACTTAAGGCGA (SEQ ID NO:11)

GTGTTGCGGTGGCGACGCTGGTCCCGATGCT

GAGTTTTGCG 3'

Where it is desired that at least two polypeptides are to be produced and secreted from a cell, it is preferable that at least two signal peptide coding sequences described in Table 1 above, are employed: one for each polypeptide. The signal peptide coding sequence may be the same, or may be different for each polypeptide to be secreted. According to yet a further aspect of the invention there are provided libraries containing random combinations of signal peptide coding sequences. Example 5 describes such libraries in more detail.

By the term "operably linked", it is meant that the nucleic acids encoding both the signal peptide and the polypeptide that is to be secreted, are under the control of a single promoter/operator region and are transcribed as a single message. Thus, an expression cassette for use in the invention can be, in its simplest form, the smallest genetic unit capable of mediating the expression and secretion of a polypeptide of interest. An expression cassette generally contains a suitable promoter/operator region (including, for example, the tac or lac or T7 or bacteriophage lambda promoter/operators for use in *E. coli*, the ecdysone responsive or human cytomegalovirus or SV40 promoters for use in mammalian cells, the Gal1 or Cup1 or AOX1 promoters for use in yeast cells, and the polyhedrin promoter for use in baculovirus), upstream of a 5' untranslated region (5'UTR), which is in turn followed by a nucleic acid encoding the signal peptide and the polypeptide to be secreted. Expression cassettes may additionally incorporate the appropriate transcriptional and translation control sequences, for example, enhancer elements, termination stop sequence, mRNA stability sequences, start and stop codons or ribosome binding sites, linked in frame with or included within, where appropriate, the nucleic acid molecules of the invention. It may be desirable for the expression cassette to remain in an episomal form within the cell. Alternatively, it may integrate into the genome of the host cell. If the latter is desired, sequences that promote recombination with the genome will be included in the expression cassette. Accordingly, further aspects of the invention provide host cells containing nucleic acids or expression cassettes as described herein and/or expressing polypeptides according to the methods described herein.

Nucleic acid sequences encoding the M13 major coat protein signal peptide, or variants thereof, may find utility in any host. For example, such bacteriophage derived signal sequences may be of value in other viral based expression systems such as, for example, baculovirus. However, prokaryotes, such as bacteria of the *Streptomyces* and *Bacillus* species, and *E. coli* are the preferred expression hosts. *E. coli* is a particularly preferred host. Where the expression host is prokaryotic, the promoter/operator region of an expression cassette will be one that is capable of regulating expression in prokaryotic hosts. As will be obvious to a person skilled in the art, if the signal peptides are to be employed in other (e.g. eukaryotic) expression systems, the promoter/operator regions will be capable of regulating expression in the specific host.

The method of the invention may additionally comprise recovering the secreted polypeptide. If the expression host is a Gram negative bacterium, the secretion process may only take the polypeptide as far as the periplasmic space. Where this is the case, the first step of any recovery procedure will be to harvest the cells (e.g. by centrifugation) and release the polypeptide from the periplasmic space. This may be achieved by disrupting the outer membrane, for example by osmotic shock or any by other suitable physically disruptive means, or by making use of host strains that have been genetically compromised and have a "leaky" outer membrane (e.g. certain strains of *E. coli* K12, see Atlan & Portarlier, 1984; Fognini Lefebvre & Portarlier, 1984). In other expression hosts, which lack an outer membrane, the polypeptide product may be secreted directly into the culture medium.

Polypeptides that have been released from the periplasmic space, or secreted to the culture medium, may be recovered and purified further using any suitable method. This includes any method which uses, for example, a difference in solubility e.g. salting out and precipitation with a solvent or, a difference in molecular weight e.g. ultrafiltration and gel electrophoresis or, a difference in electric charge e.g. ion exchange chromatography or, specific affinity e.g. affinity chromatography or, a difference in hydrophobicity e.g. reverse phase high performance liquid chromatography or, a difference in isoelectric point e.g. isoelectric focusing, to aid purification'. Further details of suitable isolation procedures and protein purification strategies will be familiar to the skilled artisan and are well documented in the art.

Nucleic acids for use herein may be generated using any standard molecular biology and/or chemistry procedure, as will be clear to those of skill in the art. Particularly suitable techniques include the oligonucleotide directed mutagenesis of the native nucleic acid encoding the M13 major coat protein signal peptide, oligonucleotide directed synthesis techniques, and enzymatic cleavage or enzymatic filling in of gapped oligonucleotides. Such techniques are described by Sambrook & Fritsch, 1989, and in the Examples contained hereinafter.

In further aspects, the nucleic acids or expression cassettes of the invention may be used with a carrier. The carrier may be a vector or other carrier suitable for the introduction of the nucleic acid/expression cassette into a host cell. Nucleic acids/expression cassettes may be sub cloned into any suitable commercially available vector (e.g. the pUC or pBluescript series of vectors for use in *E. coli*), using standard molecular biology techniques. Such vectors may include plasmids, phagemids and viruses (including both bacteriophage and eukaryotic viruses). The invention includes both cloning and expression vectors containing nucleic acids and/or expression cassettes of the invention. Where appropriate, such a vector or carrier may contain more than one expression cassette according to the invention, for example, a Fab' expression vector may contain one expression cassette encoding an antibody light chain and one expression cassette encoding an antibody heavy chain (see for example FIG. 1C).

Introduction of the nucleic acid or expression cassette into a host cell may employ any available technique. In bacterial cells, suitable techniques may include calcium chloride transformation, electroporation or transfection using bacteriophage. In eukaryotic cells suitable techniques may include calcium phosphate transfection, DEAE Dextran, electroporation, particle bombardment, liposome mediated transfection or transduction using retrovirus, adenovirus or other viruses, such as vaccinia or, for insect cells; baculovirus.

Following introduction of the nucleic acid into host cells, the cells may be cultured on a per se known medium suited for growing the host, (for example 2xYT or LB Broth for *E. coli*). Any suitable medium will usually contain at least an assimable carbohydrate, a nitrogen source and essential minerals. The carbohydrates are usually in the form of simple sugars such as lactose or glucose, the nitrogen source may include yeast extract or other sources of assimable amino acids such as tryptone, casein, phytone, peptone and beef extract. The essential minerals may vary between expression hosts but generally include trace amounts of transition metal salts such as manganese and magnesium salts. The culture medium may be modified, for example, by the addition of an antibiotic or other chemical or, by the exclusion of a particular nutrient, in order to maintain the presence of a vector or carrier within the host organism.

Growth conditions (e.g. growth medium, temperature, time and length of induction and quantity of inducing chemical if the promoter is inducible) will vary according to the individual expression system employed, but in general will be optimised in order enhance expression of the recombinant polypeptide. For example, they may be manipulated in order to allow accumulation of the expressed polypeptide in, for example, the periplasmic space or culture medium. Allowing accumulation of the polypeptide product following expression, may form an optional step in the method of the invention. General guidance with respect to growth and induction conditions, suitable for recombinant polypeptide expression, may be found in the art (see for example, Sambrook & Fritsch, 1989; Glover, 1995a,b) and specific examples of cell culture conditions and induction regimes are described herein in the following Examples.

The various aspects and embodiments of the present invention will now be illustrated in more detail by way of example. It will be appreciated that modification of detail may be made without departing from the scope of the invention.

BRIEF DESCRIPTION OF THE FIGURES

FIG. 2 Constructs to enable the production of Fab'-signal peptide libraries. A] The second copy of the tac promoter was removed as an Xho I-Xba I fragment and replaced with a Xho I-Xba I fragment carrying a tac promoter that had been modified to remove the internal Pst I and include Mfe I and Nsi I sites. B] shows the modified construct.

FIG. 3 Yield of Fab' from constructs with different signal peptide coding sequences in font of Heavy and Light chains The yield of Fab' 165 from various members of the signal peptide library having a heavy chain expression cassette followed by a light chain expression cassette, was assessed by ELISA two hours after the induction of expression. Results shown are the mean of three small scale shake flask experiments, ±SD.

FIG. 4 Effect of different signal peptide coding regions on heavy chain, light chain and total Fab' yield in fermentation. Yield was assessed by surface plasmon resonance for samples taken at 2, 13, 20 and 38 hours after the induction of expression, and is represented in terms of resonance units (RU). Data is shown for various members of the two signal peptide libraries i.e. members of the library containing a light chain expression cassette followed by a heavy chain expression cassette (LC:HC) and members of the library containing a heavy chain expression cassette followed by a light chain expression cassette (HC:LC). SP CDS=signal peptide coding sequence.

EXAMPLES

Example 1

Cloning of the Alkaline Phosphatase Gene

Figure 1:
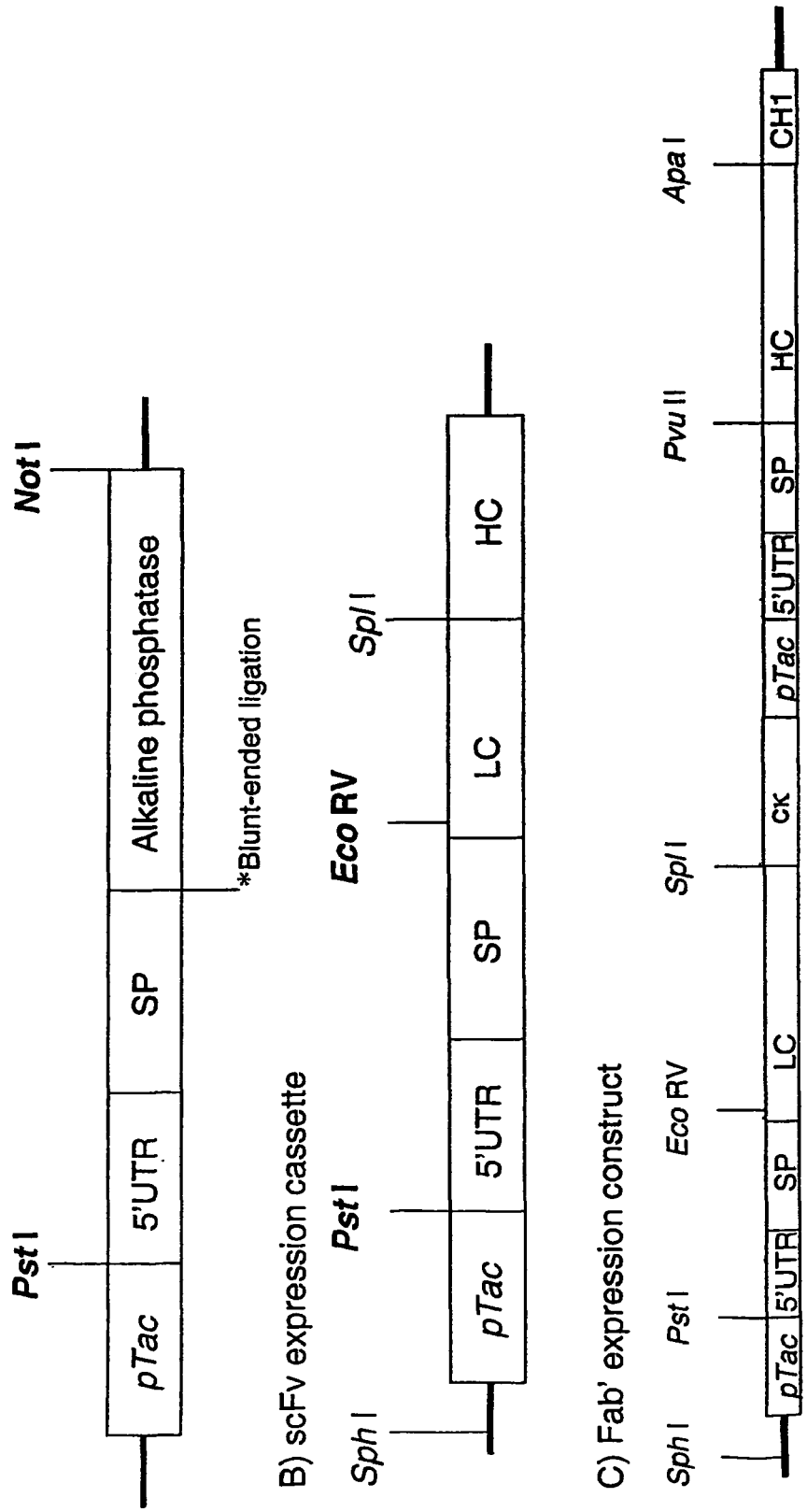
FIG. 1: Schematic Representation of Alkaline Phosphatase, scFv and Fab' Expression Cassettes. In part A) the arrangement of the alkaline phosphatase expression cassette is shown, with the signal peptide coding region (SP) ligated in-frame with the alkaline phosphatase structural gene. These are under control of the tac promoter (pTac). The position of the 5' untranslated region (5' UTR) is also shown. In part B) the arrangement of the scFv expression cassette is shown. The signal peptide (SP) is ligated in front of and in-frame with the $V_L$ coding sequence, which is subsequently linked in-frame with the $V_H$ coding sequence via a $(Gly_4Ser)_4$ linker (not shown). Expression is controlled via the tac promoter (pTac) and the position of the 5' untranslated region is also shown. In part C) the arrangement of the expression cassettes in the Fab' 40.4 expression construct is shown. Both the $V_L$ and $V_H$ coding sequences are each fused in-frame with the same signal peptide (SP) coding sequence. These are under the control of separate tac promoters (pTac). The position of the two 5' untranslated regions (5'UTR) are shown, as is the cKappa intergenic spacer ($C_K$), which separates light and heavy chain expression. The $C_{H1}$ coding region is shown fused in-frame and downstream of the $V_H$ coding region.

The phoA gene was cloned from E. coli strain W3110 by PCR, with its own signal peptide using primers PhoA1 (5' GCGCGCGCTCTGCAGGTCGAGTTCTA-GATAACGAGGCGTAAAAAA TGAAACAAAGCAC-TATTGCACTGGC 3') (SEQ ID NO: 12) and PhoA2 (5' GCGCGCGCG CGGCCGCTCATTATTTCAGCCCCA-GAGCGGCTTTCATGG 3') (SEQ ID NO: 13). The initiation codon of the native alkaline phosphatase gene was changed from GTG to the more common initiation codon of ATG. The PhoA1 primer incorporates a Pst I restriction endonuclease site at its 5' end, followed by a "5' UTR" region, the altered initiation codon and a further 23 bases of a phoA gene. The PhoA2 primer incorporates a Not I restriction endonuclease site at the 3' end of the phoA PCR product. This permits cloning of the Pst I-Not I double-digested PCR product behind any suitable promoter to form an expression cassette with the native alkaline phosphatase signal peptide.

The mature phoA gene (without its signal peptide) was cloned from E. coli strain W3110 using primers PhoA3 (5' CGGACACCAGAAATGCCTGTTCTGGAAAAC 3') (SEQ ID NO: 14) and PhoA2 (as above). This allows the cloning of the mature alkaline phosphatase gene behind any of the signal peptide cassettes described herein, as a blunt-ended/Not I fragment. Thus the efficacy of variant signal peptides and/or different nucleic acids encoding the same signal peptide amino acid sequence may be compared using alkaline phosphatase as a standard protein.

Example 2

Construction of M13 Major Coat Protein Signal Peptide Cassettes

Nucleic acid cassettes encoding the M13 major coat protein signal peptides identified in Table 1 were constructed from pairs of long complementary oligonucleotides, which were annealed at a concentration of 1 pmole/µl in buffer (25 mM NaCl, 12.5 mM Tris-HCl, 2.5 mM $MgCl_2$, 0.25 mM DTE, pH 7.5) by heating in a boiling water bath for 5 minutes and then allowing them to cool slowly to room temperature.

The design of these oligos was such that they consist of three elements: an upstream 5' UTR region, a core encoding the signal peptide and a downstream linker region to permit subsequent cloning of the signal peptide into an expression cassette in front of the gene encoding the polypeptide that was to be secreted. As the skilled man will appreciate, the sequence of this linker may be varied in order to adapt these signal peptide cassettes for use with other polypeptides. Cassettes encoding signal peptides that were used to direct secretion of alkaline phosphatase lacked the downstream linker and consisted of the 5' UTR and the core signal peptide coding region only.

Example 3

Construction of Expression Vectors with the M13 Major Coat Protein Signal Peptide Encoded by Different Nucleic Acids Alkaline phosphatase expression vectors: Signal peptide cassettes that had been constructed by annealing oligonucleotides (see Example 2 above), were ligated to Not I digested mature PhoA PCR product (described in Example 1 above), producing a Pst I-Not I fragment. This was then ligated into vector behind the tac promoter (see FIG. 1A).

scFv expression vectors: To enable the facile introduction of new signal peptide coding regions, an EcoR V restriction endonuclease site was introduced in the first two codons of the $V_L$ domain of an existing scFv expression plasmid [see for example the International Patent Specification No. WO 01/94585] This plasmid contains a scFv specific for a human cytokine, in the $V_L$-$V_H$-His organisation, under control of the tac promoter. The scFv also contains a (Gly$_4$Ser)$_4$ linker. Signal peptide cassettes that had been constructed by annealing oligonucleotides (see Example 2 above) were then ligated into Pst I-EcoR V double digested scFv expression vector (see FIG. 1B).

Fab' expression vectors: Vectors for expressing Fab' light and heavy chains under the dual control of tac promoters were constructed as follows. The $V_L$ expression cassette within an existing Fab' expression vector [see for example the International Patent Specification No. WO 01/94585] was excised by double digestion with Pst I and Spl I restriction endonucleases, and replaced by SP-$V_L$ cassettes, that had been similarly excised from the scFv expression vectors described above. The SP-$V_H$ fragments were created and introduced as PCR fragments using a short reverse 3' oligonucleotide that anneals in the $C_{H1}$ region, and long 5' forward oligonucleotides that encode the signal peptide. This resulted in a series of Fab' 40.4 expression vectors containing the different signal peptides in front of the 40.4 light and heavy chains. These vectors were advantageously designed such that there are unique restriction sites at the 5' and 3' borders of the $V_L$ and $V_H$ regions (EcoR V-Spl I, Pvu II-Apa I) respectively, thus enabling rapid exchange of variable domain and/or signal peptide coding regions (see FIG. 1C).

Control expression vectors for both Fab' and scFv were constructed by replacing the M13 signal peptides with the *E. coli* OmpA signal peptide.

Example 4

Heterologous Polypeptide Expression and Secretion Using M13 Major Coat Protein Signal Peptide a) Methods Polypeptide Production in Liquid Culture—Production of Alkaline Phosphatase and scFv in Shake Flask.

Shake flask experiments and extraction of periplasmic fractions were conducted essentially as described previously (Humphreys et al 1996), with tetracycline being employed at a final concentration of 10 μg/ml in the growth medium. Polypeptide expression was induced by the addition of IPTG to 0.2 mM and assayed, either by enzyme assay or ELISA as appropriate, at time points between 0 and 5 hours post-induction.

Polypeptide Expression Liquid Culture—Production of Fab' by Fermentation.

Fermentations were run in media 'SM6E': (NH$_4$)$_2$SO$_4$ 5.2 gL$^{-1}$; NaH$_2$PO$_4$.H$_2$O 4.14 gL$^{-1}$; KCl 4.025 gL$^{-1}$; MgSO$_4$.7H$_2$O 1.04 gL$^{-1}$; citric acid 5.20 gL$^{-1}$; glycerol 31.111 gL$^{-1}$; CaCl$_2$.2H$_2$O 0.0522 gL$^{-1}$; ZnSO$_4$.7H$_2$O 0.0206 gL$^{-1}$; MnSO$_4$.4H$_2$O 0.0272 gL$^{-1}$; CuSO$_4$.5H$_2$O 0.0081 gL$^{-1}$; CoSO$_4$.7H$_2$O 0.0042 gL$^{-1}$; FeCl$_3$.6H$_2$O 0.1006 gL$^{-1}$; H$_3$BO$_3$ 0.0003 gL$^{-1}$; Na$_2$MoO$_4$.2H$_2$O 0.0002 gL$^{-1}$; MAZU DF843 as an antifoam at 0.02% (v/v), and the pH made to 6.95 with NH$_4$OH. Fermentors (Braun BiostatB 2.5 L) were inoculated with sufficient seed culture (in SM6E media supplemented with tetracycline at 10 μgml$^{-1}$) to give an initial OD$_{600}$ of 0.2. The pH was controlled by the addition of 50% (v/v) NH$_4$OH and 1.8M H$_2$SO$_4$ as necessary, and the dissolved oxygen was maintained at 30% using variable agitation and airflow. Cultures were batch fed with 2×45 ml 80% (w/w) glycerol at OD$_{600}$ 20 and 40 respectively. Fab' expression was induced at an OD$_{600}$ of approximately 80 by exhaustion of glycerol and substitution of lactose as the carbon source. Lactose concentration was maintained at between 20 and 50 gL$^{-1}$ throughout the production phase, and cells were harvested 24-36 hours post-induction.

Fermentation cell pastes were resuspended in ½ harvest volume of 100 mM Tris.HCl/10 mM EDTA pH7.4 and agitated at 250 rpm, 30° C. for 16 hours. Periplasmic extracts were clarified by centrifugation at 25,000 g for 30 minutes and passed through a 0.2 μm filter (Millipore), before purification on Protein G Sepharose (GammaBind Plus, Pharmacia Biotech) as described previously (Humphreys et al., 1998).

Assay for Alkaline Phosphatase Activity

Assays were performed as essentially as described previously (Humphreys et al., 1995), with the following modifications: expression was induced by 0.2 mM IPTG, and assays were performed on 20 μl of culture approximately 3 hours post induction. Alkaline phosphatase activity was expressed as $\Delta A_{420}$ OD$_{600}^{-1}$ min$^{-1}$.

ELISA of scFv and Fab' Concentration in Shake Flask and Fermentation Periplasmic Extracts.

For scFv ELISA Nunc Maxisorp plates were coated with antigen (a human cytokine) at 0.5 μgml$^{-1}$ in 100 mM sodium bicarbonate buffer pH 9.0 for 16 hours at 4° C. After washing 4 times in blocking buffer (0.1% w/v BSA in PBS), and twice in glazing buffer (10% w/v trehalose, 0.1% w/v BSA in PBS) the plates were air dried and stored in sealed foil pouches at 4° C. Purified standard was diluted to 250 ngml$^{-1}$, followed by serial two-fold dilutions, in 1% w/v BSA in PBS. Each well was incubated with 100 μl of sample or standard and agitated at room temperature for 1 hour. After washing twice with 0.0002% w/v Tween20 in PBS, each well was incubated with 100 μl of rabbit anti-His tag antibody (Santa Cruz Biotech, Cat. no. SC-803) diluted ⅟500 in 1% w/v BSA in PBS and agitated at room temperature for 30 minutes. After washing twice with 0.0002% w/v Tween20 in PBS, each well was incubated with 100 μl of donkey anti-rabbit HRP (Jackson, Cat. no. 711-035-152) diluted ⅟5000 in 1% w/v BSA in PBS and agitated at room temperature for 30 minutes. The plate was then washed 4 times with 0.0002% w/v Tween20 in PBS and developed as previously (Humphreys et al. 1996). ELISA to assess Fab' concentration was performed as described by Humphreys et al. (1996).

Accuracy of Cleavage of Signal Peptide in Front of Alkaline Phosphatase.

Periplasmic extracts were produced from *E. coli* expressing and secreting alkaline phosphatase using the MCP3 signal peptide. These extracts were analysed by SDS-PAGE using 4-20% Trisglycine gels (Novex) according to manufacturers instructions. Proteins were transferred from the polyacrylamide gel to PVDF membrane (PSQ, Applied Biosystems), by elctroblotting in 10 mM CAPS (3-cyclohexylamino-1-propanesulfonic acid, Sigma) pH 11.0, then stained with Ponceau S. The band corresponding to alkaline phosphatase was excised, and the protein eluted for N-terminal sequence analysis.

b) Results.

Expression and Secretion of Alkaline Phosphatase

TABLE 2

Alkaline phosphatase activity in liquid culture 3 hours post-induction.

| Signal peptide | Alkaline phosphatase activity ($\Delta A_{420}$ $OD_{600}^{-1}$ $min^{-1}$ ± S.D. n = 3) |
|---|---|
| MCP1 | 0.91 ± 0.16 |
| MCP2 | 4.90 ± 1.01 |
| MCP3 | 4.82 ± 1.07 |
| MCP4 | 4.68 ± 0.21 |
| MCP5 | 4.31 ± 0.10 |
| MCP6 | 4.27 ± 0.49 |
| MCP7 | 4.21 ± 0.78 |
| MCP8 | 3.61 ± 0.70 |
| MCP9 | 3.52 ± 1.23 |
| OmpA control | 5.17 ± 0.58 |

Alkaline phosphatase expression was observed from all ten M13 major coat protein signal peptide constructs, although some differences in the level of expression were observed between constructs whose M13 signal peptides were encoded by nucleic acid variants. In general the level of expression observed was similar to that obtained with the control signal peptide OmpA (see Table 2 above).

A MCP3-containing clone expressing alkaline phosphatase was arbitrarily chosen to assess the accuracy of signal peptide cleavage, as described in Example 4 above. N-terminal sequencing revealed that the signal peptide cleavage site had been correctly recognised resulting in the correct N-terminal sequence for mature alkaline phosphatase.

Expression and Secretion of scFv

The ability of four of the variants as well as the native M13 major coat protein signal peptide were assessed for their ability to secrete scFv to the periplasm of E. coli by ELISA. The OmpA signal peptide was also employed for comparative purposes. The results are shown in Table 3 below.

TABLE 3

Yield of scFv in shake flask liquid culture 2.5 hours post-induction.

| Signal peptide | scFv yield ng ml$^{-1}$ $OD_{600}^{-1}$ ± S.D. (n = 3) |
|---|---|
| MCP1 | 220.0 ± 63.7 |
| MCP3 | 189.5 ± 17.1 |
| MCP4 | 185.0 ± 31.6 |
| MCP8 | 185.5 ± 8.0 |
| MCPn | 264.0 ± 22.2 |
| OmpA control | 147.8 ± 14.0 |

Expression and Secretion of Fab"

The ability of the four variants assessed for their ability to secrete scFv, as well as the native M13 major coat protein signal peptide were also assessed for their ability to secrete Fab' to the periplasm of E. coli. Clones were grown and expression induced under the fermentation conditions described above. The yield of purifed Fab' was assessed by ELISA and the results are shown in Table 4 below.

TABLE 4

Yield of purified Fab' from fermentation.

| Signal peptide | Yield of Purified Fab" (mg/L) |
|---|---|
| MCP1 | 35 |
| MCP3 | 227 |
| MCP4 | 383 |
| MCP8 | 178 |
| MCPn | 94 |
| OmpA control | 67 |

Again, the M13 Major coat protein was shown to be successful at expressing and secreting high levels of Fab'. Surprisingly some of the nucleic acid variants were shown to be more efficacious than the OmpA control. The results demonstrate that the level of expression can be increased approximately five-fold over that produced by the control signal peptide by using in this instance the MCP4 variant nucleic acid to encode the M13 Major coat protein signal peptide.

Expression and Secretion of Different Fab' Molecules

The M13 bacteriohage signal peptide can be used to direct the secretion of different Fab' molecules. To demonstrate this, the VH and VL regions in each of MCP1, MCP3, MCP4 and MCP8 Fab' 40.4 constructs were excised as Eco RV-Spl I and Pvu II-Apa I fragments respectively, and replaced with similarly digested $V_H$ and $V_L$ regions from an antibody that recognises a different antigen to that recognised by Fab' 40.4. Four master constructs were thus produced to enable the expression of the new Fab'; each construct used a different nucleotide sequence to encode the M13 bacteriophage signal peptide in front of the light and heavy chains (NB the same nucleotide sequence was used for the light and heavy chain within a single construct) and each contained a light chain expression cassette followed by a heavy chain expression cassette (see FIG. 1C).

The expression and secretion of the Fab' molecule (Fab' 165) was assessed under the fermentation conditions described in Example 4 above. The yield of purifed Fab' was assessed by ELISA and the results are shown in Table 5 below:

TABLE 5

Yield of different Fab' fragments from fermentation

| Nucleotide sequence encoding signal peptide | Yield of Purified Fab' 165 (mg/L) |
|---|---|
| MCP1 | 369 |
| MCP3 | 134 |
| MCP4 | 189 |
| MCP8 | 437, 316 |

Example 5

Optimisation of Fab' Expression

In the Examples described above, the nucleotide sequence encoding the M13 bacteriophage signal peptide has been the same for both the light and heavy chain in each Fab' expression construct. In order to assess the effect, on expression and secretion, of combinations of the different signal peptide encoding nucleotide sequences within the same construct, two plasmid libraries were constructed. Each library contained all 16 possible combinations of the MCP1, MCP3, MCP4 and MCP8 sequences in front of the light and heavy chains of Fab' 165.

a) Construction of Fab' Plasmid Library Containing VL Expression Cassette Followed by VH Expression Cassette

TABLE 6

The sixteen possible combinations of the different signal peptide coding sequence are shown in the matrix below. The first expression cassette is represented along the top, and the second expression cassette is represented down the side. These constructs all have a light chain expression cassette followed by a heavy chain expression cassette.

| HEAVY CHAIN | mcp1 | mcp1-VL-mcp1-VH | mcp3-VL-mcp1-VH | mcp4-VL-mcp1-VH | mcp8-VL-mcp1-VH |
|---|---|---|---|---|---|
| | mcp3 | mcp1-VL-mcp3-VH | mcp3-VL-mcp3-VH | mcp4-VL-mcp3-VH | mcp8-VL-mcp3-VH |
| | mcp4 | mcp1-VL-mcp4-VH | mcp3-VL-mcp4-VH | mcp4-VL-mcp4-VH | mcp8-VL-mcp4-VH |
| | mcp8 | mcp1-VL-mcp8-VH | mcp3-VL-mcp8-VH | mcp4-VL-mcp8-VH | mcp8-VL-mcp8-VH |

Starting with the four master Fab' 165 constructs described in Example 4 above, these were digested with Pst I and Mfe I, and the fragments and vector backbones allowed to recombine randomly, thus resulting in all 16 possible combinations of signal peptide coding sequence as shown in Table 6.

b) Construction of Fab' Plasmid Library Containing VH Expression Cassette Followed by VL Expression Cassette.

Since Pst I is compatible with Nsi I and Mfe I is compatible with Eco RI (see FIG. 2), each of the four Fab' 165 master constructs produced in Example 4 above, was treated as follows. A first sample of each construct was digested with Nsi I and Eco RI and the signal peptide coding sequence and Heavy chain fragment was isolated. A second sample of each construct was digested with Pst I and Mfe I, and both fragments isolated and purified. The Heavy chain fragment from the first digestion was ligated with the vector backbone (lacking a light chain fragment) from the second, to produce a construct containing two heavy chains. This construct was then digested with Nsi I and Eco RI to remove the second signal peptide coding sequence and Heavy chain. The small Heavy chain fragment was discarded and the remaining vector backbone (containing a 5' Heavy chain fragment) was ligated to a mixture of the signal peptide and light chain fragments from the second digestion.

as described previously. Levels of expression of light chains, heavy chains and total Fab' was assessed using surface plasmon resonance and/or ELISA.

Surface plasmon resonance binding assays were performed using a BIAcore™ 2000 instrument (Pharmacia Biosensor AB, Uppsala, Sweden). Murine IgG2a monoclonal anti-human IgG Pan Fd (CH1), obtained from hybridoma HP6045 (ATCC) and murine IgG2a monoclonal anti-human kappa light chain constant domain ($C_\kappa$), obtained from hybridoma HP6053 (ATCC) was immobilised onto CM5 sensor chips using standard NHS/EDC chemistry. Residual NHS esters were inactivated with ethanolamine hydrochloride (1 M).

Fab' fragments were captured by either an immobilised monoclonal anti-heavy chain or by an immobilised monoclonal anti-light chain antibody in separate flow cells. The presence of bound Fab' was revealed by binding of the complementary monoclonal antibody (anti-light chain or anti-heavy chain) in a second step. High levels of immobilised antibody ensure that measurements are performed under mass transport-limited conditions, where the contribution of the association rate constant to binding is low in comparison to the contribution made by the concentration of the Fab' in the sample. The solution phase monoclonal antibody used in the second step is passed over the surface

TABLE 7

The sixteen possible combinations of the different signal peptide coding sequence are shown in the matrix below. The first expression cassette is represented along the top, and the second expression cassette is represented down the side. These constructs all have a heavy chain expression cassette followed by a light chain expression cassette.

| | | mcp1 | mcp3 | mcp4 | mcp8 |
|---|---|---|---|---|---|
| LIGHT CHAIN | mcp1 | mcp1-VH-mcp1-VL | mcp3-VHmcp1-VL | mcp4-VH-mcp1-VL | mcp8-VH-mcp1-VL |
| | mcp3 | mcp1-VH-mcp3-VL | mcp3-VH-mcp3-VL | mcp4-VH-mcp3-VL | mcp8-VH-mcp3-VL |
| | mcp4 | mcp1-VH-mcp4-VL | mcp3-VH-mcp4-VL | mcp4-VH-mcp4-VL | mcp8-VH-mcp4-VL |
| | mcp8 | mcp1-VH-mcp8-VL | mcp3-VHmcp8-VL | mcp4-VH-mcp8-VL | mcp8-VH-mcp8-VL |

Thus a library of 16 constructs were produced having the order of the light and heavy chain expression cassettes reversed from that in the library described in a) above. Table 7 shows the combinations of signal peptides present in the library c) Analysis of Fab' 165 Expression Expression studies were carried out in small scale shake flasks as described previously. Following on from the result obtained at this scale, the ability of several of the different clones to express Fab' was assessed in fermentations, again at a high concentration so that binding is not limited by the association rate constant of this interaction.

Assembled Fab' fragments and correctly folded unassembled chains are both detected during the first capture step. Binding of the second antibody is only to an intact Fab' fragment. Therefore, analysis of the relative binding at the first and second stages reveals the presence of either excess unassembled light chain, or excess unassembled heavy chain in the Fab' sample and provides information on the stoichiometry of assembly.

Assays were performed in both configurations for each sample, and each sample was run in duplicate and in a randomised order.

(i) Where the concentration of assembled Fab' was to be determined by light chain capture, samples and standards (10 μl at 10 μl/min) were injected over immobilised HP6053, followed by a second step in which HP6045 at 300 μg/ml was passed over the surface in the solution phase.

(ii) Where the concentration of assembled Fab' was to be determined by heavy chain capture, samples and standards (10 μl at 10 μl/min) were injected over immobilised HP6045, followed by a second step in which HP6053 at 500 μg/ml was passed over the surface in the solution phase. In both cases, the surface was regenerated with 10 μl of 30 mM HCl at 30 μl/min.

The number of resonance units determined using the BIAevaluation 3.1 (Pharmacia Biosensor AB), was read against a standard curve. There was a linear response from 2 μg/ml down to 50 ng/ml purified Fab' standard.

FIG. 3 shows that the level of Fab' expression varies considerably between different constructs having the expression cassettes in the heavy chain-light chain order. Similar results were obtained for light chain-heavy chain library (data not shown). Thus the two libraries containing different combinations of signal peptide coding sequences can be used to optimise Fab' expression. Using Eco RV-Spl I and Pvu II-Apa I double digestions, the light and heavy chains of other antibodies can be substitute for those of Fab' 165, and thus the libraries can be used to optimise the expression of any Fab' molecule.

FIG. 4 compares the yield of each chain and total Fab' during the course of a fermentation run for various combinations of signal peptide coding sequences. It is surprising that the yield of total Fab' is maximal when the levels of expression of heavy and light chains are closely balanced. Thus Fab' expression can be optimised using the signal peptide libraries to achieve a balance between light and heavy chain expression and this forms a further aspect of the invention, particularly when each signal sequence is under the control of its own promoter/operator.

REFERENCES:

Atlan, D. & Portarlier, R. 1984 *Applied Microbiology & Biotechnology* 19:5-12.

Fognini Lefebvre, N. & Portarlier, R. *FEMS Microbiology Letters* 21:323 328.

Glover, D. M. 1995a. *DNA cloning: a practical approach, Volume II: Expression systems*. IRL press.

Glover, D. M. 1995b. *DNA cloning: a practical approach, Volume IV: Mammalian systems*. IRL press.

Humphreys, D. P., Weir, N., Mountain, A. & Lund, P. A. 1995. *Journal of Biological Chemistry* 270:28210-28215.

Humphreys, D. P. Weir, N., Lawson, A., Mountain, A. & Lund, P. A. 1996 *FEBS Letts.* 380:194-197.

Humphreys, D. P., Vetterlein, O. M., Chapman, A. P., King, D. J., Antoniw, P., Suitters, A. J., Reeks, D. G., Parton, T. A. H., King, L. M., Smith, B. J., Lang, V. & Stephens, P. E. (1998) *Journal of Immunological Methods* 217:1-10.

Gray, G. L., Baldridge, J. S., McKeown, K. S., Heyneker, H. L. & Chang, C. N. 1985. *Gene* 39:247 254.

Kumagai, M. H., Shah, M., Terashima, M., Vrkljan, Z., Whitaker, J. R. & Rodriguez, R. L. 1990 *Gene* 94:209 216.

Sambrook, J. & Fritsch, E. 1989 *Molecular cloning: a laboratory manual.* 2nd edition. Cold Spring Harbour Press, N.Y.

The invention claimed is:

1. A method of producing an antibody chain or an antigen binding fragment thereof, comprising culturing *E. coli* host cells containing an expression cassette under conditions that result in expression of the antibody chain, or fragment thereof, from the expression cassette, wherein said expression cassette comprises a first nucleic acid encoding the native bacteriophage M13 major coat protein signal peptide operably linked to and in frame with a second nucleic acid encoding the antibody chain or antigen binding fragment thereof.

2. A method according to claim 1, wherein the first nucleic acid, encoding the native bacteriophage M13 major coat protein signal peptide amino acid sequence, differs in the nucleotide sequence from the native M13 nucleotide sequence.

3. A method according to claim 2, wherein the first nucleic acid has the nucleotide sequence of MCP1, MCP3, MCP4, MCP5, MCP6, MCP7, MCP8, or MCP9.

4. A method according to claim 3, wherein the first nucleic acid has the nucleotide sequence of MCP1, MCP3, MCP4, or MCP8.

5. A method for producing a whole antibody or a fragment thereof which comprises producing an antibody heavy chain according to claim 1 and an antibody light chain according to claim 1 and allowing the chains to assemble.

6. A method according to claim 5 in which the heavy and light chain are produced in the same host cell from separate expression cassettes.

7. A method according to claim 6 in which each expression cassette is under the control of a single promoter/operator.

8. A method according to claim 6 or claim 7 in which each signal peptide is selected to achieve a balanced expression of heavy and light chains.

9. A method according to any one of claims 1, or 2-7, which further comprises a) optionally, allowing the antibody, antibody fragment, antibody chain or antigen binding fragment to accumulate and b) isolating the antibody, antibody fragment, antibody chain or antigen binding fragment.

10. A nucleic acid encoding the native bacteriophage M13 major coat protein signal peptide wherein the nucleotide sequence of said nucleic acid is selected from MCP1, MCP3, MCP4, MCP5, MCP6, MCP7, MCP8, or MCP9.

11. A nucleic acid according to claim 10, wherein the nucleotide sequence of the M13 major coat protein signal peptide is selected from MCP1, MCP3, MPC4, or MCP8.

12. An expression cassette comprising a first nucleic acid according to claim 10, operably linked to and in frame with a second nucleic acid encoding an antibody chain or antigen binding fragment thereof.

13. A vector comprising a nucleic acid according to claim 10 or one or two expression cassettes according to claim 12.

14. A host cell containing an expression cassette according to claim 12.

15. A host cell containing a vector according to claim 13.

* * * * *